United States Patent
Mizutani et al.

(10) Patent No.: US 7,182,846 B2
(45) Date of Patent: Feb. 27, 2007

(54) HYDROGEN-CONTAINING GAS MEASUREMENT SENSOR ELEMENT AND MEASURING METHOD USING SAME

(75) Inventors: Keigo Mizutani, Okazaki (JP); Masataka Naito, Kariya (JP); Daisuke Makino, Ichinomiya (JP); Kazunori Suzuki, Nagoya (JP)

(73) Assignees: Denso Corporation (JP); Nippon Soken, Inc. (JP)

( * ) Notice: Subject to any disclaimer, the term of this patent is extended or adjusted under 35 U.S.C. 154(b) by 700 days.

(21) Appl. No.: 10/447,303

(22) Filed: May 29, 2003

(65) Prior Publication Data

US 2003/0221975 A1 Dec. 4, 2003

(30) Foreign Application Priority Data

May 29, 2002 (JP) ............................. 2002-156241
Mar. 28, 2003 (JP) ............................. 2003-090476

(51) Int. Cl.
*G01N 27/26* (2006.01)

(52) U.S. Cl. ...................... 204/427; 204/424; 204/426; 204/431

(58) Field of Classification Search ............... 204/424, 204/425, 426, 427, 431, 432; 205/783.5, 205/787
See application file for complete search history.

(56) References Cited

U.S. PATENT DOCUMENTS

| | | | |
|---|---|---|---|
| 5,672,811 A | 9/1997 | Kato et al. | |
| 5,866,799 A | 2/1999 | Kato et al. | |
| 5,879,525 A | 3/1999 | Kato | |
| 5,939,615 A | 8/1999 | Kato et al. | |
| 6,076,393 A | 6/2000 | Kato et al. | |
| 6,196,053 B1 | 3/2001 | Kato et al. | |
| 6,517,702 B2 * | 2/2003 | Stahl | 205/784.5 |
| 2001/0010290 A1 | 8/2001 | Taniguchi | |
| 2003/0121800 A1 | 7/2003 | Wahl et al. | |

FOREIGN PATENT DOCUMENTS

| | | |
|---|---|---|
| JP | 8-247995 | 9/1996 |
| JP | 8-271476 | 10/1996 |

(Continued)

OTHER PUBLICATIONS

Japanese Office Action dated Oct. 3, 2006 in Japanese Patent Application No. 2003-090476 together with English translation.

*Primary Examiner*—Nam Nguyen
*Assistant Examiner*—Luan V. Van
(74) *Attorney, Agent, or Firm*—Nixon & Vanderhye, PC (57) ABSTRACT

A gas sensor element is provided which is designed to measure the concentration of hydrogen-containing gas accurately. The sensor element includes an oxygen pump cell working to keep the concentration of oxygen contained in measurement gasses entering a measurement gas chamber at a low concentration level and a hydrogen-containing gas measurement cell. The hydrogen-containing gas measurement cell is made up of a proton-conductive solid electrolyte body and a first and a second gas measurement electrode affixed to the proton-conductive solid electrolyte body. The first gas measurement electrode is exposed to the measurement gas chamber and serves to produce a signal between the first and second gas measurement electrodes as a function of the concentration of the hydrogen-containing gas.

19 Claims, 10 Drawing Sheets

FOREIGN PATENT DOCUMENTS

| | | |
|---|---|---|
| JP | 2000-283959 | 10/2000 |
| JP | 2000-292409 | 10/2000 |
| JP | 2001-50933 | 2/2001 |
| JP | 2001-141690 | 5/2001 |
| JP | WO 01/48466 | 7/2001 |
| JP | 2002277430 | 9/2002 |

\* cited by examiner

HYDROGEN-CONTAINING GAS MEASUREMENT SENSOR ELEMENT AND MEASURING METHOD USING SAME

BACKGROUND OF THE INVENTION

1. Technical Field of the Invention

The present invention relates generally to a gas sensor element for use in measuring the concentration of hydrogen-containing gasses including hydrogen atom-made compounds such as hydrocarbon, hydrogen, and moisture and a measuring method using the same.

2. Background Art

The air population arising from automobile exhaust fumes has posed serious problems with modern life. The emission regulation, thus, has become severe year by year.

More effective emission purification is expected to be achieved by measuring the concentration of hydrocarbon gas contained in the exhaust emissions and feeding it back to an engine burning control monitoring system or a catalyst monitoring system. Accordingly, some hydrocarbon sensor elements have been proposed in the prior art which are capable of determining the concentration of hydrocarbon gas contained in exhaust emissions of automotive vehicles precisely.

Figure 12:
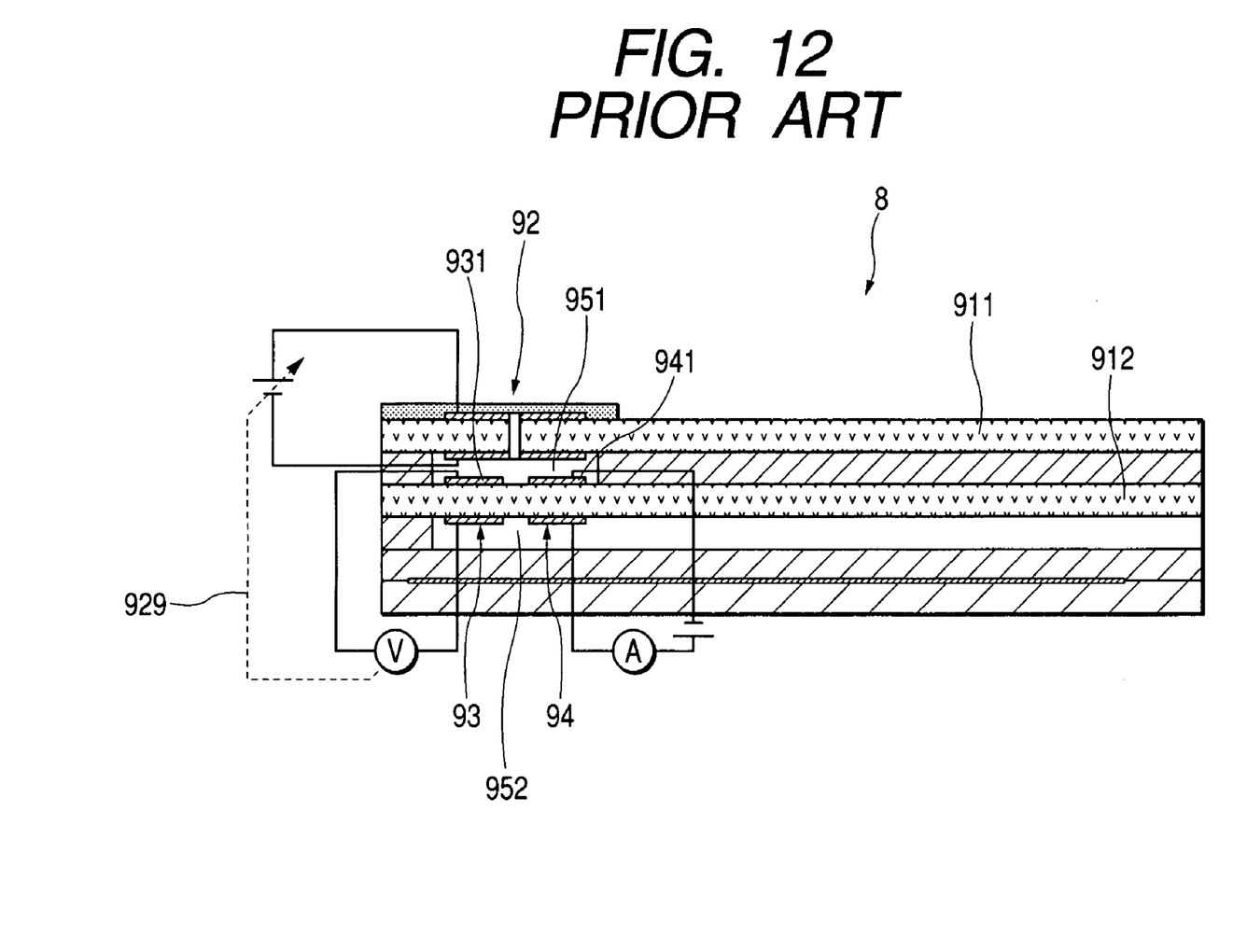
FIG. 12 is a longitudinal sectional view which shows a conventional gas sensor element.

FIG. 12 shows a conventional hydrocarbon sensor element 8.

The hydrocarbon sensor element 8 consists essentially of a measurement gas chamber 951 into which exhaust gasses to be measured are admitted and an oxygen pump cell 92 exposed to the measurement gas chamber 951. Application of voltage to the oxygen pump cell 92 causes oxygen molecules to be pumped out of the measurement gas chamber 951 into the ambient atmosphere or vice versa.

The hydrocarbon sensor element 8 also includes an oxygen monitor cell 93 which works to monitor the concentration of oxygen within the measurement gas chamber 951 and produce an electromotive force indicative thereof. A feedback circuit 929 monitors the output of the oxygen monitor cell 93 and controls the voltage applied to the oxygen pump cell 92 so as to keep the concentration of oxygen within the measurement chamber 951 substantially constant.

The oxygen monitor cell 93 has an electrode 931 exposed to the measurement gas chamber 951 which is made of a material that is highly active to oxidize hydrocarbon, thereby enabling the oxygen monitor cell 93 to measure the amount of oxygen remaining after reaction of the hydrocarbon with the oxygen on the electrode 931.

The hydrocarbon sensor element 8 also includes a sensor cell 94 exposed to the measurement gas chamber 951. The sensor cell 94 has an electrode 941 which is exposed to the measurement gas chamber 951 and made of a material that is hardly active to oxidize the hydrocarbon. This causes the oxygen to be excessive on the electrode 941 as compared with around the electrode 931 of the oxygen monitor cell 93. This excessive oxygen is drained from the measurement gas chamber 951 to a reference gas chamber 952 by applying the voltage to the sensor cell 94, thereby causing an oxygen ion current to be produced as an output of the sensor cell 94 which is proportional to entration of hydrocarbon contained in the measurement gasses (i.e., automobile exhaust gasses).

Reference numbers 911 and 912 denote oxygen ion-conductive solid electrolyte bodies.

The hydrocarbon sensor element 8 is, as apparent from the above discussion, designed to use a difference in oxidation activity between the electrodes to measure the concentration of hydrocarbon as a function of an oxygen ion current arising from a difference in concentration of oxygen between the electrodes, thus resulting in a change in sensor output due to a change in concentration of oxygen contained in the measurement gasses or aging of activity of the electrodes. This problem is common to gas sensors designed to measure the concentration of hydrogen-containing gas containing a hydrogen compound such as hydrogen gas or moisture in the same manner as described above.

SUMMARY OF THE INVENTION

It is therefore a principal object of the invention to avoid the disadvantages of the prior art.

It is another object of the invention to provide a gas sensor element capable of measuring the concentration of a hydrogen-containing gas with high accuracy and a hydrogen-containing gas measuring method.

According to one aspect of the invention, there is provided a gas sensor element which may be employed in measuring the concentration of a hydrogen-containing gas contained in exhaust emissions of automotive vehicles. The gas sensor element comprises: (a) a measurement gas chamber into which measurement gasses enter, subjected to a given diffusion resistance; (b) an oxygen pump cell working to control a concentration of oxygen contained in the measurement gasses within the measurement gas chamber, the oxygen pump cell including an oxygen ion-conductive solid electrolyte body and a first and a second oxygen pump electrode affixed to the oxygen ion-conductive solid electrolyte body, the first oxygen pump electrode being exposed to the measurement gas chamber; and (c) a hydrogen-containing gas measurement cell working to measure a concentration of a hydrogen-containing gas contained in the measurement gasses within the measurement gas chamber. The hydrogen-containing gas measurement cell includes a proton-conductive solid electrolyte body and a first and a second gas measurement electrode affixed to the proton-conductive solid electrolyte body. The first gas measurement electrode is exposed to the measurement gas chamber and serves to produce a signal between the first and second gas measurement electrodes as a function of the concentration of the hydrogen-containing gas.

The use of the proton-conductive solid electrolyte body in the hydrogen-containing gas measurement cell enables protons to be dissociated on the first gas measurement electrode from the hydrogen-containing gas, i.e., a hydrogen-containing compound in the measurement gasses, thereby resulting in a flow of electrical current through the proton-conductive solid electrolyte body as a function of the number of the protons.

Usually, the proton-conductive solid electrolyte body does not exhibit the pure proton conductivity and permits the current to flow which arises from the hole and oxygen ion conduction in the presence of oxygen. The oxygen pump cell is capable of keeping the concentration of oxygen within the measurement gas chamber at a lower level, thereby suppressing the hole and oxygen ion conduction to minimize the current produced by the hole and oxygen ion conduction to improve the accuracy of determining the concentration of the hydrogen-containing gas.

In the preferred mode of the invention, the oxygen pump cell is located upstream of the hydrogen-containing gas measurement cell in a flow of the measurement gasses within the measurement gas chamber, thereby enabling the gasses reaching the hydrogen-containing gas measurement cell to be kept low in concentration of oxygen, which achieves the high measurement accuracy for the reason as described above.

The gas sensor element may further comprise a second hydrogen-containing gas measurement cell exposed to the measurement gas chamber for measuring the concentration of a different hydrogen-containing gas.

The second hydrogen-containing gas measurement cell may include a proton-conductive solid electrolyte body and a first and a second gas measurement electrode affixed to the proton-conductive solid electrolyte body. The first gas measurement electrode is exposed to the measurement gas chamber and serves to produce an electrical current between the first and second gas measurement electrodes as a function of concentration of the hydrogen-containing gas contained within the measurement gasses which is different in kind from the hydrogen-containing gas to be measured by the hydrogen-containing gas measurement cell. The concentration of the hydrogen-containing gas, as measured by the hydrogen-containing gas measurement cell, is indicated as a function of an electrical current produced between the first and second measurement electrodes of the hydrogen-containing gas measurement cell, and the concentration of the hydrogen-containing gas, as measured by the second hydrogen-containing gas measurement cell, is indicated as a function of a difference between the electrical currents produced by the hydrogen-containing gas measurement cell and the second hydrogen-containing gas measurement cell.

The hydrogen-containing gas measurement cell and the second hydrogen-containing gas measurement cell may be arrayed in substantially the same position in the flow of the measurement gasses within the measurement gas chamber and symmetrical in configuration with respect to the flow of the measurement gasses, thereby minimizing adverse effects arising from the distribution of the measurement gases within the measurement gas chamber.

The proton-conductive solid electrolyte body may be formed by a perovskite type oxide made in matrix structure from at least one of $SrZrO_3$, $CaZrO_3$, $SrCeO_3$, and $BaCeO_3$. Such a proton-conductive solid electrolyte body ensures the stability of operation of the hydrogen-containing gas measurement cell within a high temperature range of 600 to 900° C. that are temperatures of automobile exhaust gasses and also facilitates ease of use with an oxygen ion-conductive solid electrolyte body such as zirconia which is active in a similar high temperature range.

One of Y, Yb, Sc, In, Gd, Dy, and Sm may be substituted for either of Zr and Ce in the matrix structure of the proton-conductive solid electrolyte body.

An oxygen monitor cell may further be provided which works to measure a concentration of oxygen in the measurement gasses.

The oxygen pump cell may be so controlled as to keep an electrical current or voltage produced by the oxygen monitor cell constant.

Voltages which are different in level from each other may be applied to the hydrogen-containing gas measurement cell and the second hydrogen-containing gas measurement cell to produce outputs indicative of the concentrations of the hydrogen-containing gasses, thereby enabling protons to be dissociated from desired hydrogen-containing gasses.

The oxygen monitor cell includes an oxygen ion-conductive solid electrolyte body and a first and a second monitor electrodes affixed to the oxygen ion-conductive solid electrolyte body. The first monitor electrode is exposed to the measurement gas chamber and made of a material which is low in oxidizing activity.

The first oxygen pump electrode of the oxygen pump cell, the first gas measurement electrode of the hydrogen-containing gas measurement cell, and the first monitor electrode of the oxygen monitor cell which are exposed to the measurement gas chamber are each made of a material which is low in oxidizing activity, thereby avoiding burning of the hydrogen-containing gas caused by combination of the hydrogen-containing gas with oxygen on the electrodes.

The first oxygen pump electrode of the oxygen pump cell, the first gas measurement electrode of the hydrogen-containing gas measurement cell, and the first pump electrode of the oxygen monitor cell which are exposed to the measurement gas chamber may be each made from a material containing in principal component at least one of Pt, Pd, and Rh and at least one of Au, Cu, Pb and Ti.

One of Au, Cu, Pb, and Ti lies in content within a range of 1 to 30% of a total weight of each of the electrodes in terms of oxidation activity and the ability of pumping oxygen and protons in the oxygen pump cell, the hydrogen-containing gas measurement cell, and the oxygen monitor cell.

The gas sensor element may further include a NOx measurement cell which includes an oxygen ion-conductive solid electrolyte body and a first and a second NOx measurement electrodes affixed to the oxygen ion-conductive solid electrolyte body. The first NOx measurement electrode is exposed to the measurement gas chamber and active with NOx contained in the measurement gasses, the NOx measurement cell producing an electrical current as a function of a concentration of NOx contained in the measurement gasses.

A difference between the electrical currents produced by the oxygen monitor cell and the NOx measurement cell may be used in determining the concentration of NOx contained in the measurement gasses, thereby minimizing an oxygen-caused measurement error.

According to the second aspect of the invention, there is provided a gas measuring method which comprises the steps of: (a) introducing measurement gasses into a measurement gas chamber while being subjected to a given diffusion resistance; (b) controlling an electrical current flowing through an oxygen pump cell made up of an oxygen ion-conductive solid electrolyte body and a first and a second pump electrode affixed to the oxygen ion-conductive solid electrolyte body to pump oxygen molecules selectively into and out of the measurement gas chamber to regulate a concentration of oxygen within the measurement gas chamber, the first pump electrode being exposed to the measurement gas chamber; and (c) measuring an electrical current flowing through a hydrogen-containing gas measurement cell made up of a proton-conducive solid electrolyte body and a first and a second gas measurement electrode affixed to the proton-conductive solid electrolyte body to determine a concentration of a given hydrogen-containing gas contained in the measurement gasses. The first gas measurement electrode is exposed to the measurement gas chamber.

According to the third aspect of the invention, there is provided a gas measuring method which comprises the steps of: (a) introducing measurement gasses into a measurement gas chamber while being subjected to a given diffusion resistance; (b) controlling an electrical current flowing through an oxygen pump cell made up of an oxygen ion-conductive solid electrolyte body and a first and a second pump electrode affixed to the oxygen ion-conductive solid electrolyte body to pump oxygen molecules selectively into and out of the measurement gas chamber to regulate a concentration of oxygen within the measurement gas chamber, the first pump electrode being exposed to the measurement gas chamber; (c) measuring an electrical current flowing through a first hydrogen-containing gas measurement cell made up of a proton-conducive solid electrolyte body and a first and a second gas measurement electrode affixed to the proton-conductive solid electrolyte body to determine a concentration of a first hydrogen-containing gas contained in the measurement gasses, the first gas measurement electrode being exposed to the measurement gas chamber; and (d) measuring an electrical current flowing through a second hydrogen-containing gas measurement cell made up of a proton-conducive solid electrolyte body and a first and a second gas measurement electrode affixed to the proton-conductive solid electrolyte body to determine a concentration of a second hydrogen-containing gas contained in the measurement gasses. The first gas measurement electrode is exposed to the measurement gas chamber. The second hydrogen-containing gas is different in kind from the first hydrogen-containing gas.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figures 1A, 1B:
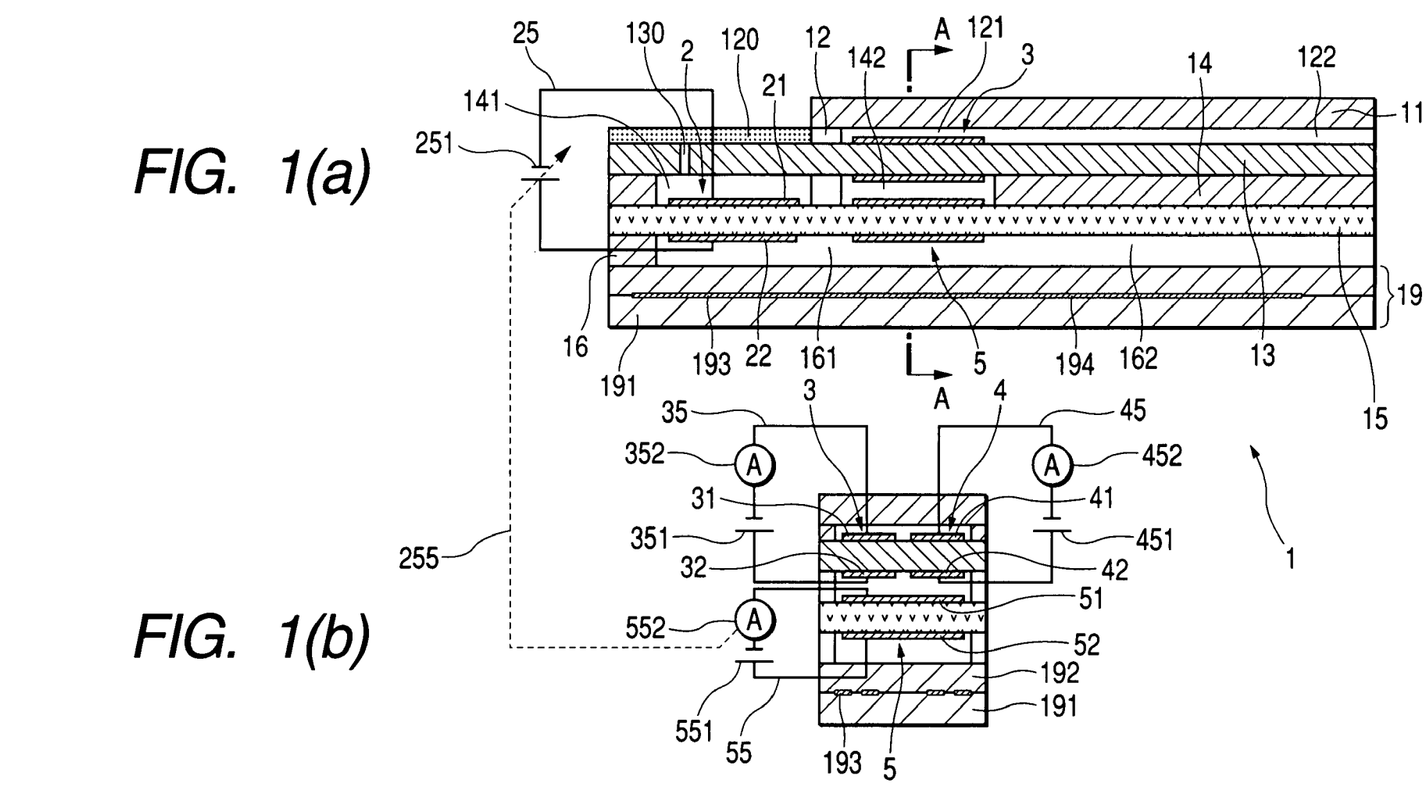
FIG. 1(a) is a longitudinal sectional view which shows a gas sensor element according to the first embodiment of the invention.
FIG. 1(b) is a transverse sectional view as taken along the line A—A in FIG. 1(a)
Figure 2:
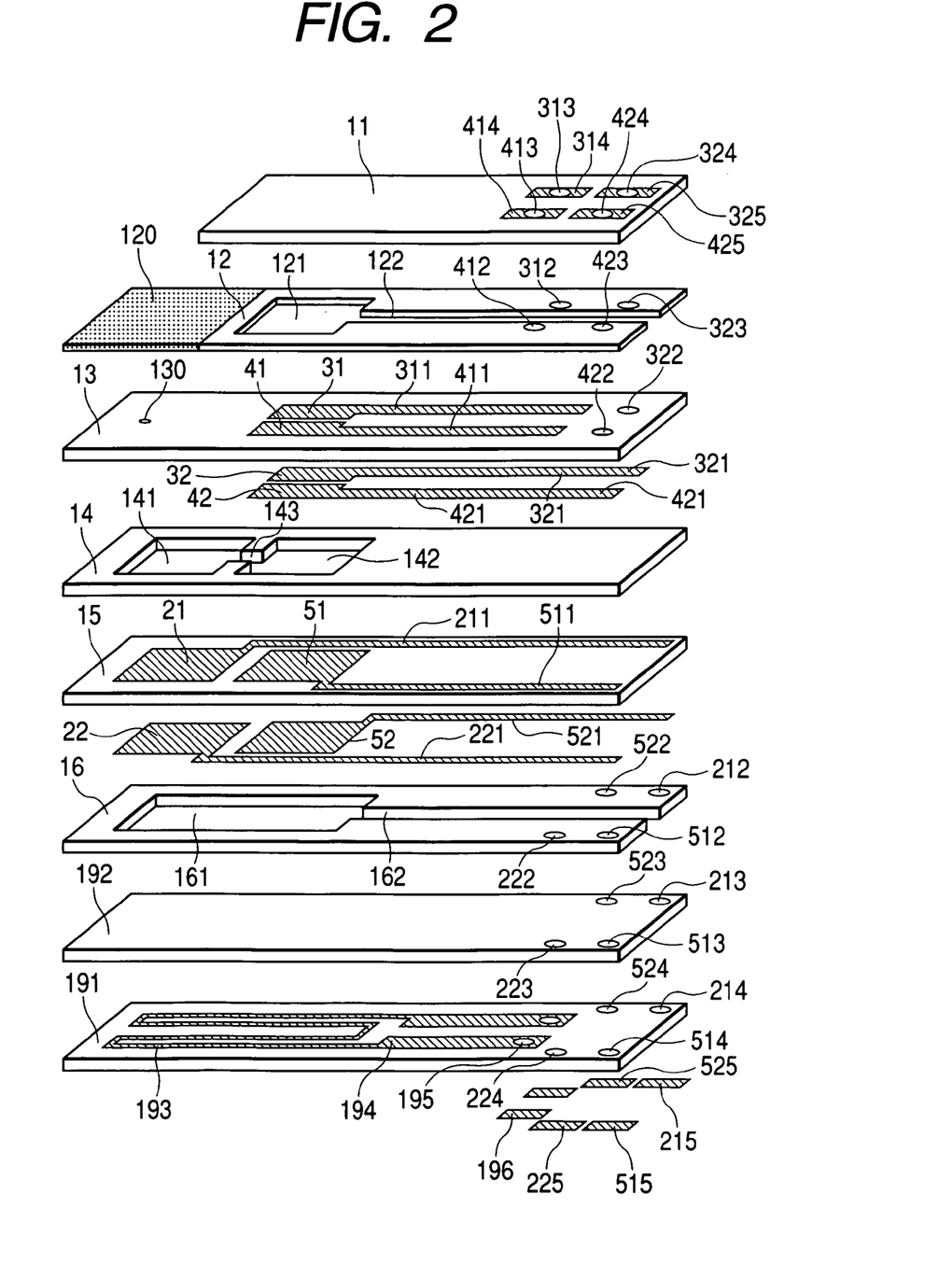
FIG. 2 is an exploded view which shows the gas sensor element of FIG. 1(a)

Referring to the drawings, wherein like reference numbers refer to like parts in several views, particularly to FIGS. 1(a), 1(b), and 2, there is shown a gas sensor element 1 according to the first embodiment of the invention which may be installed in an exhaust pipe of an internal combustion engine to measure concentrations of a hydrocarbon (HC) gas and a hydrogen gas contained in exhaust emissions of the engine for use in engine burning control and/or catalytic systems.

The gas sensor element 1 includes generally first and second measurement gas chambers 141 and 142 into which gases to be measured (will also be referred to as measurement gases below) are introduced, subjected to a given diffusion resistance, an oxygen pump cell 2 exposed to the first measurement gas chamber 141, and first and second hydrogen-containing gas measurement cells 3 and 4 exposed to the second measurement gas chamber 142. The oxygen pump cell 2 is made up of an oxygen ion-conductive solid electrolyte plate 15, an electrode 21 exposed to the first measurement gas chamber 141, and an electrode 22 which are affixed to the solid electrolyte plate 15. The oxygen pump cell 2 works to reduce and dissociate or ionize oxygen molecules ($O_2$) contained in the exhaust gasses existing outside the gas sensor element 1 and pump them into the first measurement gas chamber 141 and also to dissociate or ionize and pump the oxygen molecules ($O_2$) outside the first measurement gas chamber 141 when the concentration of oxygen within the first measurement gas chamber 141 is higher than a given level for keeping the concentration of oxygen within the first measurement gas chamber 141 (and the second measurement gas chamber 142) at the given level.

The first and second hydrogen-containing gas measurement cells 3 and 4 are made up of a proton-conductive solid electrolyte plate 13, hydrogen-containing gas measurement electrodes 32 and 42 exposed to the second measurement gas chamber 142, and electrodes 31 and 41, respectively. The electrodes 32, 42, 31, and 41 are affixed to opposed surfaces of the solid electrolyte plate 13. The first and second hydrogen-containing gas measurement cells 3 and 4 work to measure the concentration of hydrogen-containing gases within the second gas measurement gas chamber 142.

The gas sensor element 1 is, as can be seen from FIG. 2, made of a laminate of insulating plates 11, 12, 14, and 16, the proton-conductive solid electrolyte plate 13, and the oxygen ion-conductive solid electrolyte plate 15. The gas sensor element 1 also includes a ceramic heater 19 attached to the insulating plate 16 which works to heat the cells 2, 3, 4, and 5 up to a desired activation temperature.

The gas sensor element 1 also includes an oxygen monitor cell 5. The first and second measurement gas chambers 141 and 142 communicate with each other through an orifice 143. The orifice 143 works as a diffusion resistor and will also be referred to as a diffusion resistance path below.

The oxygen pump cell 2 is, as described above, exposed to the first measurement gas chamber 141. The oxygen monitor cell 5 and the first and second hydrogen-containing gas measurement cells 3 and 4 are exposed to the second measurement gas chamber 142. The oxygen pump cell 2 and the oxygen monitor cell 5 are also exposed to a first reference gas chamber 161. The first and second hydrogen-containing gas measurement cells 3 and 4 are also exposed to a second reference gas chamber 121.

The first measurement gas chamber 141 is located in a gas flow upstream of the second measurement gas chamber 142. Thus, the oxygen pump cell 2 is located on the upstream side, while the first and second hydrogen-containing gas measurement cells 3 and 4 are located on the downstream side.

The first and second hydrogen-containing gas measurement cells 3 and 4 are located in the same position in a lengthwise direction of the gas sensor element 1. Specifically, they are arrayed in parallel to each other along a direction of flow of the measurement gases at the same distance from a gas inlet 130.

The gas inlet 130 is formed by a pin hole and establishes communication between the first measurement gas chamber 141 and the inside of the exhaust pipe of the engine to introduce the measurement gases into the first measurement gas chamber 141.

The proton-conductive solid electrolyte plate 13 has disposed thereon a diffusion resistance layer 120 made of a porous ceramic material, for example, which covers the gas inlet 130.

The first and second reference gas chambers 161 and 121 lead to the ambient atmosphere.

The insulating plate 16 works as a spacer to define the first reference gas chamber 161 and an air passage 162 leading to the ambient atmosphere. Similarly, the insulating plate 14 works as a spacer to define the second measurement gas chamber 142. The insulating plate 12 works as a spacer to define the second reference gas chamber 121 and the air passage 122 leading to the ambient atmosphere.

The insulating plates 11, 12, 14, and 16 are each made of a dense, gas-impermeable alumina ceramic. The oxygen ion-conductive solid electrolyte plate 15 is made of partially-stabilized zirconia. The proton-conductive solid electrolyte plate 13 is formed by a perovskite type oxide made in matrix structure from at least one of $SrZrO_3$, $CaZrO_3$, $SrCeO_3$, and $BaCeO_3$. One of Y, Yb, Sc, In, Gd, Dy, and Sm may be substituted for either of Zr and Ce in at least a part of the matrix structures of the proton-conductive solid electrolyte plate 13. The diffusion resistance layer 120 is a gas-permeable alumina ceramic having a high porosity.

The oxygen pump cell 2, as described above, has the electrodes 21 and 22. The electrode 21 is exposed to the first measurement gas chamber 141. The electrode 22 is exposed to the first reference gas chamber 161.

The oxygen pump cell 2 connects electrically with a pump circuit 25 equipped with a variable power supply 251. Application of voltage to the electrodes 21 and 22 through the power supply 251 will cause an oxygen ion current to flow between the electrodes 21 and 22 which works to pump oxygen molecules into the first measurement gas chamber 141 from the first reference gas chamber 161 or vice versa.

Specifically, the variable power supply 251 connects, as clearly shown in FIG. 1, at a positive terminal to the pump electrode 22 and at a negative terminal to the pump electrode 21 to reduce and dissociate or ionize oxygen molecules contained in the measurement gases on the pump electrode 21 to produce oxygen ions which are, in turn, pumped or transferred to the pump electrode 22. A feedback controller 255 works to monitor the concentration of oxygen within the second measurement gas chamber 142 as measured by the oxygen monitor cell 5 and regulate the voltage to be applied to the oxygen pump cell 2 so as to keep the concentration of oxygen within the second measurement gas chamber 142 at a given low-concentration value. For example, the feedback controller 255 may control the voltage applied to the oxygen pump cell 2 so as to keep the electrical current or voltage produced by the oxygen monitor cell 5 constant.

The electrode 21 of the oxygen pump cell 2 is, as shown in FIG. 2, connected electrically to a terminal 215 through a lead 211 and conductive holes 212, 213, and 214. These conductive holes are coated at an inner wall thereof, for example, with a conductive material. Similarly, the electrode 22 is connected electrically to a terminal 225 through a lead 221 and conductive holes 222, 223, and 224.

The pump electrode 21 is made of a Pt—Au cermet. The pump electrode 22 is made of a Pt cermet.

The oxygen monitor cell 5 has a pair of monitor electrodes 51 and 52 affixed to opposed surfaces of the oxygen ion-conductive solid electrolyte plate 15. The monitor electrode 51 is exposed to the second measurement gas chamber 142. The monitor electrode 52 is exposed to the first reference gas chamber 161. The oxygen monitor cell 5 connects electrically to a monitor circuit 55 equipped with a power supply 551 and a current detector 552. The power supply 551 works to apply a voltage of, for example, 0.40V to the monitor electrodes 51 and 52 to produce flow of an oxygen iron current therebetween as a function of concentration of oxygen molecules within the second measurement gas chamber 142. The current detector 552 works to measure the oxygen iron current for determination of the oxygen concentration in the second measurement gas chamber 142.

The monitor electrode 51 is, as shown in FIG. 2, connected electrically to a terminal 515 through a lead 511 and conductive holes 512, 513, and 514. Similarly, the monitor electrode 52 is connected electrically to a terminal 525 through a lead 521 and conductive holes 522, 523, and 524.

The monitor electrode 51 is made of a Pt—Au cermet. The monitor electrode 52 is made of a Pt cermet.

Specifically, the power supply 551 connects, as clearly shown in FIG. 1(b), at a positive terminal to the monitor electrode 52 and at a negative terminal to the monitor electrode 51 to reduce and dissociate or ionize oxygen molecules contained in the measurement gases on the monitor electrode 51 to produce oxygen ions which are, in turn, pumped or transferred to the monitor electrode 52. Specifically, the oxygen monitor cell 5 is a limiting current concentration cell designed to produce a limiting current as a function of the concentration of oxygen.

The feedback controller 255 disposed between the pump circuit 255 and the monitor circuit 55, as already described, works to monitor the concentration of oxygen within the second measurement gas chamber 142 through the current detector 552 and regulate the voltage to be applied to the oxygen pump cell 2 so as to keep the concentration of oxygen within the second measurement gas chamber 142 at a given low-concentration value.

As described above, the first and second measurement gas chambers 141 and 142 are kept in oxygen concentration at a low-concentration value, thus preventing the hydrogen-containing gas from being burnt and transformed into water prior to measurement of the hydrogen-containing gas through the first and second hydrogen-containing gas measurement cells 3 and 4.

The material of $SrZr_{0.9}Yb_{0.1}O_{2.95}$ forming the proton-conductive solid electrolyte plate 13 does not exhibit the pure proton conductivity and permits the current to flow which arises from the hole and oxygen ion conduction in the presence of oxygen. The pure proton conduction is, therefore, established by pumping the oxygen molecules through the oxygen pump cell 2 and the oxygen monitor cell 5 to suppress the hole and oxygen ion conduction, thereby resulting in improved accuracy of determining the concentration of the hydrogen-containing gas.

The hydrogen-containing gas measurement cell 3 has a pair of electrodes 31 and 32 affixed to opposed surfaces of the proton-conductive solid electrolyte plate 13. The electrode 32 is exposed to the second measurement gas chamber 142. The electrode 31 is exposed to the second reference gas chamber 121.

The first hydrogen-containing gas measurement cell 3 connects electrically to a first measurement circuit 35 equipped with a power supply 351 and a current detector 352. The power supply 351 works to apply the voltage to the electrodes 31 and 32, thereby causing hydrogen atoms to be dissociated from the hydrogen-containing gas in the measurement gasses on the electrode 32 exposed to the second measurement gas chamber 142 to produce protons. The protons are then transferred through the proton-conductive solid electrolyte plate 13 to the electrode 31. This causes the electrical current to flow through the first hydrogen-containing gas measurement cell 3 as a function of the quantity of hydrogen-containing gas dissolved on the electrode 32. Specifically, the magnitude of the electrical current flowing through the first hydrogen-containing gas measurement cell 3 as measured by the current detector 352 indicates the concentration of hydrogen-containing gas contained in the measurement gasses.

The electrode 31 of the first hydrogen-containing gas measurement cell 3 is, as shown in FIG. 2, connected electrically to a terminal 314 through a lead 311 and conductive holes 312 and 313. Similarly, the electrode 32 is connected electrically to a terminal 325 through a lead 321 and conductive holes 322, 323, and 324.

The second hydrogen-containing gas measurement cell 4 is substantially identical in structure and operation with the first hydrogen-containing gas measurement cell 3. Specifically, the second hydrogen-containing gas measurement cell 4 has a pair of electrodes 41 and 42 affixed to opposed surfaces of the proton-conductive solid electrolyte plate 13. The electrode 42 is exposed to the second measurement gas chamber 142. The electrode 41 is exposed to the second reference gas chamber 121.

The second hydrogen-containing gas measurement cell 4 connects electrically to a second measurement circuit 45 equipped with a power supply 451 and a current detector 452.

The electrode 41 of the second hydrogen-containing gas measurement cell 4 is, as shown in FIG. 2, connected electrically to a terminal 414 through a lead 411 and conductive holes 412 and 413. Similarly, the electrode 42 is connected electrically to a terminal 425 through a lead 421 and conductive holes 422, 423, and 424.

The first and second hydrogen-containing gas measurement cells 3 and 4 work to measure the concentration of a hydrocarbon (HC) gas and a hydrogen gas contained in the measurement gasses.

If the voltage to be applied to the first hydrogen-containing gas measurement cell 3 is 0.3V, and the voltage to be applied to the second hydrogen-containing gas measurement cell 4 is 0.5V, the electrode 32 of the first hydrogen-containing gas measurement cell 3 works to dissociate hydrogen atoms almost only from hydrogen gas to produce protons, while the electrode 42 of the second hydrogen-containing gas measurement cell 4 works to dissociate atoms from the hydrogen and hydrocarbon gasses to produce protons. Therefore, the concentration of hydrogen gas contained in the measurement gasses is determined by the first hydrogen-containing gas measurement cell 3, while the concentration of hydrocarbon gas is determined as a function of a difference between electrical currents produced in the first and second hydrogen-containing gas measurement cells 3 and 4. The voltage required to decompose moisture is high as much as approximately 1V, thus resulting in almost no decomposition of the moisture in the cells 3 and 4.

The gas sensor element 1 is, as described above, equipped with the ceramic heater 19 laminated to the body of the gas sensor element 1. The oxygen ion-conductive solid electrolyte plate 15 and the proton-conductive solid electrolyte plate 13 usually exhibit desired electrical conductivity when heated above a given activation temperature. The ceramic heater 19, thus, works to heat the oxygen ion-conductive solid electrolyte plate 15 and the proton-conductive solid electrolyte plate 13 up to the given activation temperature to set the gas sensor element 1 active in operation.

The ceramic heater 19 is, as illustrated in FIG. 2, made up of a heater substrate 191, a heating element 193, a lead 194, a terminal 196 affixed to the heater substrate 191, and a cover substrate 192 affixed to the heater substrate 191. The heater substrate 191 has conductive through hole 195 which establish electrical connection between the lead 194 and the terminal 196. The heater substrate 191 and the cover plate 192 are each made of an alumina ceramic. The heating element 193 is formed by cermet made of Pt and an insulating ceramic such as alumina. Similarly, the lead 194 and the terminal 196 are formed by cermet made of Pt and insulating ceramic such as alumina.

As already described, the first and second hydrogen-containing gas measurement cells 3 and 4 are constructed using the proton-conductive solid electrolyte plate 13, thus causing protons to be dissociated from hydrocarbon and hydrogen gasses contained in the measurement gasses which result in flows of electrical current through the proton-conductive solid electrolyte plate 13 as a function of the number of the protons. A determination of concentration of the hydrogen-containing gas within the measurement gasses may, therefore, be made directly by measuring either or both of the electrical currents flowing in the first and second hydrogen-containing gas measurement cells 3 and 4, which provides improvement in the measurement accuracy as compared with conventional indirect measurement.

The proton-conductive solid electrolyte plate 13, as described above, does not exhibit the pure proton conductivity and creates both the hole and oxygen ion conductions in the presence of oxygen. The gas sensor element 1 has the oxygen pump cell 2 exposed to the first measurement gas chamber 141 to keep the concentration of oxygen within the first and second measurement gas chambers 141 and 142 at a lower level, thereby suppressing the hole and oxygen ion conductions contributing to measurement errors of the gas sensor element 1. Specifically, the gas sensor element 1 is designed to create the pure proton conduction to produce flows of electrical current through the first and second hydrogen-containing gas measurement cells 3 and 4, thus ensuring the accuracy of measuring the concentration of hydrogen-containing gases such as hydrocarbon and hydrogen gasses.

The oxygen pump 2 opens to the first measurement gas chamber 141 located on the upstream side in gas flow, while the first and second hydrogen-containing gas measurement cells 3 and 4 open to the second measurement gas chamber 142 located on the downstream side, so that the measurement gasses are already controlled in concentration by the oxygen pump cell 2 to a lower level before reaching the first and second hydrogen-containing gas measurement cells 3 and 4, thus resulting in further improved accuracy of determining the concentration of hydrogen-containing gasses.

The use of voltages of 0.3V and 0.5V applied to the first and second hydrogen-containing gas measurement cells 3 and 4, as described above, causes the electrode 32 of the first hydrogen-containing gas measurement cell 3 to dissociate hydrogen atoms almost only from hydrogen gas to produce protons and the electrode 42 of the second hydrogen-containing gas measurement cell 4 to dissociate atoms from the hydrogen and hydrocarbon gasses to produce protons. This enables the concentration of hydrogen gas contained in the measurement gasses to be determined by the first hydrogen-containing gas measurement cell 3 and the concentration of hydrocarbon gas to be determined as a function of a difference between electrical currents produced in the first and second hydrogen-containing gas measurement cells 3 and 4.

Figures 3A, 3B:
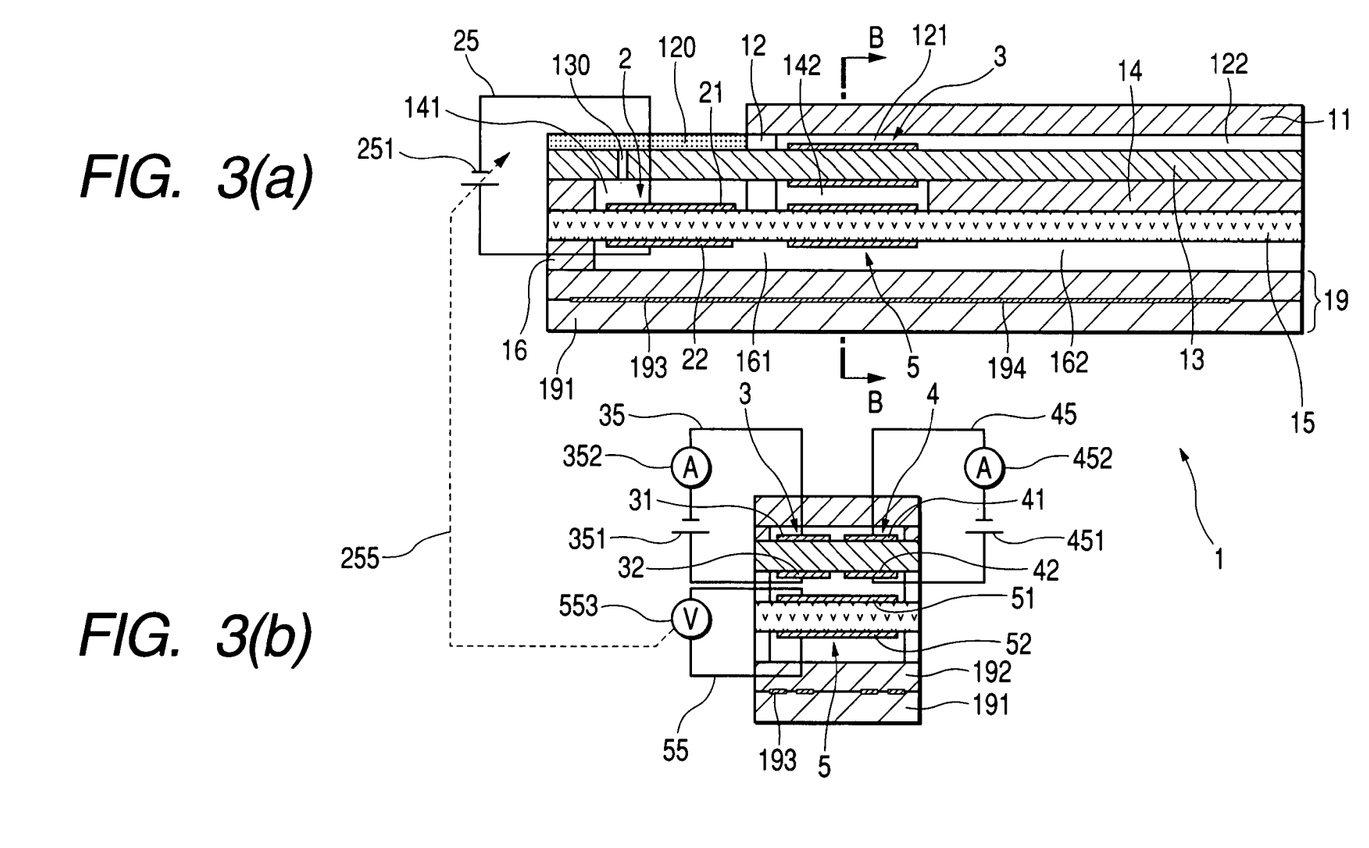
FIG. 3(a) is a longitudinal sectional view which shows a gas sensor element according to the second embodiment of the invention.
FIG. 3(b) is a transverse sectional view as taken along the line B—B in FIG. 3(a)

FIGS. 3(a) and 3(b) show the gas sensor element 1 according to the second embodiment of the invention which is designed to develop an electromotive force at the electrodes 51 and 52 of the oxygen monitor cell 5 as a function of concentration of oxygen within the measurement gases.

The oxygen monitor cell 5 connects electrically to the monitor circuit 55 equipped with a voltmeter 553. The electrode 51 of the oxygen monitor cell 5 is exposed to the second measurement gas chamber 142, while the electrode 52 is exposed to the first reference gas chamber 161. The electromotive force is creased, as expressed by the Nernst's equation, between the electrodes 51 and 52 as a function of a difference in concentration of oxygen between the second measurement gas chamber 142 and the first reference gas chamber 161. The first reference gas chamber 161 is kept constant in concentration of oxygen, so that the electromotive force produced between the electrodes 51 and 52 indicates the concentration of oxygen within the second measurement gas chamber 142.

Therefore, the concentration of oxygen within the second measurement gas chamber 142 may be maintained at a lower level by controlling the voltage applied to the oxygen pump cell 2 so as to bring the electromotive force produced between the electrodes 51 and 52 into agreement with a given value, e.g., 0.40V.

Other arrangements and operation are identical with those in the first embodiment, and explanation thereof in detail will be omitted here.

Figures 4A, 4B:
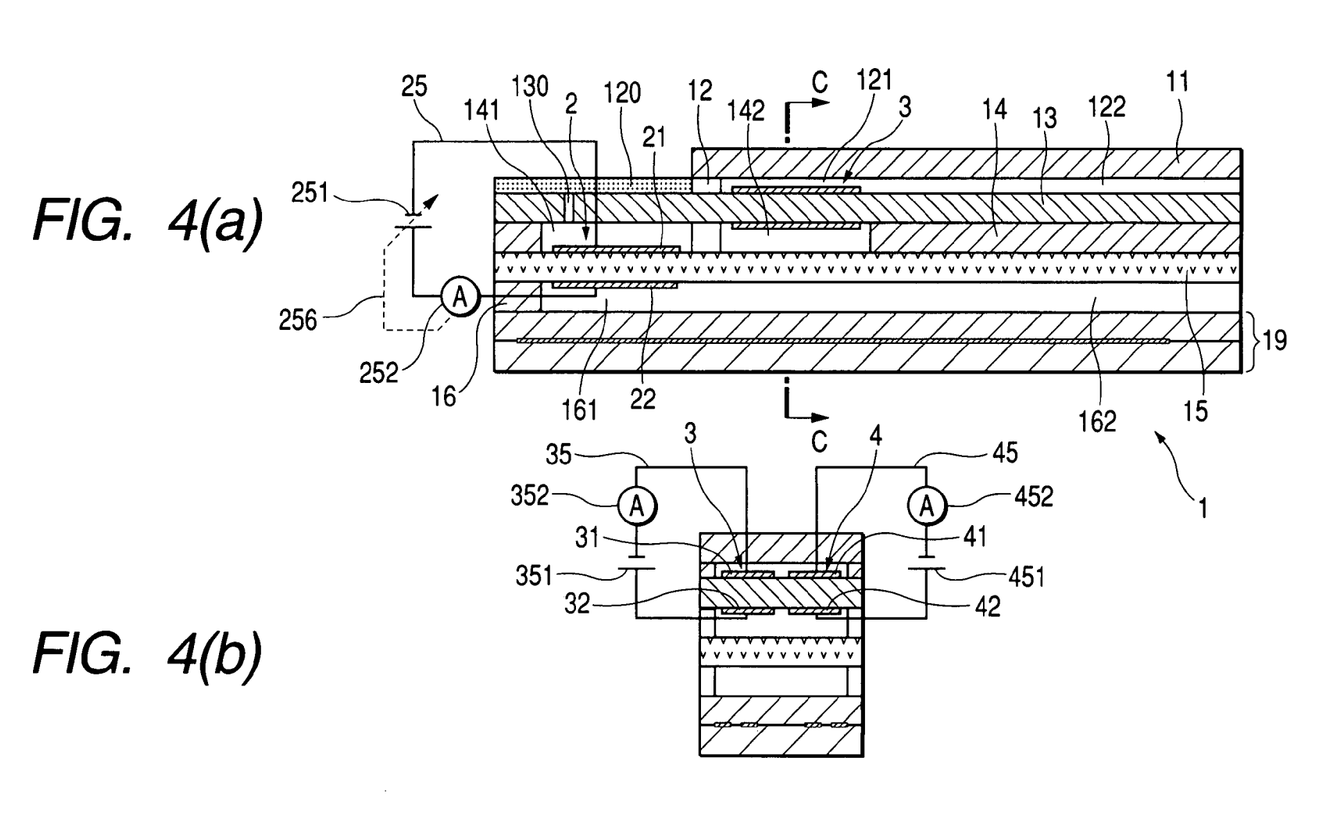
FIG. 4(a) is a longitudinal sectional view which shows a gas sensor element according to the third embodiment of the invention.
FIG. 4(b) is a transverse sectional view as taken along the line C—C in FIG. 4(a)

FIGS. 4(a) and 4(b) show the gas sensor element 1 according to the third embodiment of the invention which has a three-cell structure equipped with the oxygen pump cell 2 and the first and second hydrogen-containing gas measurement cells 3 and 4.

Specifically, the gas sensor element 1 of this embodiment is identical in structure with the one of the first embodiment from which the oxygen monitor cell 5 is removed. The feedback control circuit 256 is disposed between the current detector 252 of the pump circuit 25 connecting to the oxygen pump cell 2 and the variable power supply 251.

Figure 5:
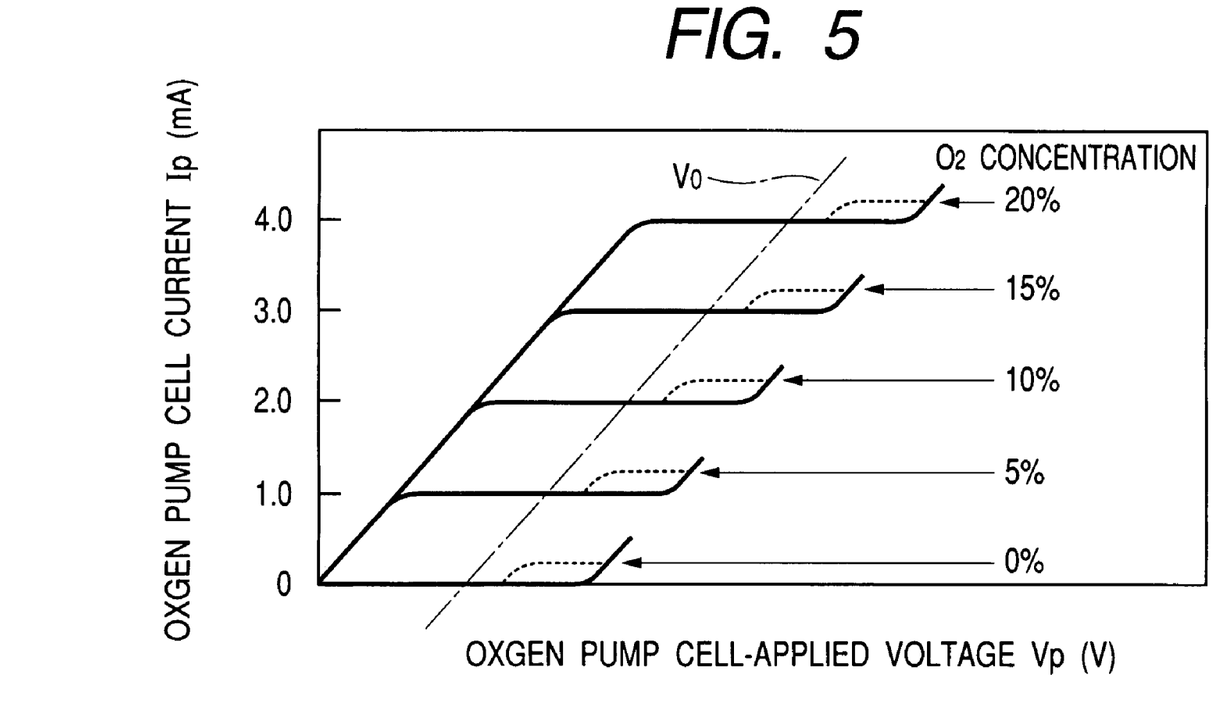
FIG. 5 is a graph which shows a relation between voltage applied to an oxygen pump cell and a resulting electrical current produced by the oxygen pump cell.

FIG. 5 illustrates a relation between voltage Vp applied to the oxygen pump cell 2 and the resulting current Ip flowing through the oxygen pump cell 2. The graph shows that the oxygen pump cell 2 produces the constant current Ip as a function of the concentration of oxygen within a given limiting current range defined by a portion of each curve extending parallel to an abscissa axis (i.e., a Vp-axis). The limiting current range is shifted to a positive side of the pump cell-applied voltage Vp as the concentration of oxygen increases.

In operation, the feedback control circuit 256 works to monitor the oxygen pump current Ip through the current detector 252 and regulate the voltage Vp applied to the oxygen pump cell 2 so as to make the oxygen pump cell 2 produce the limiting current, thereby keeping the concentration of oxygen within the first measurement chamber 141 at a lower level.

Other arrangements and operation are identical with those in the first embodiment, and explanation thereof in detail will be omitted here.

Figures 6A, 6B:
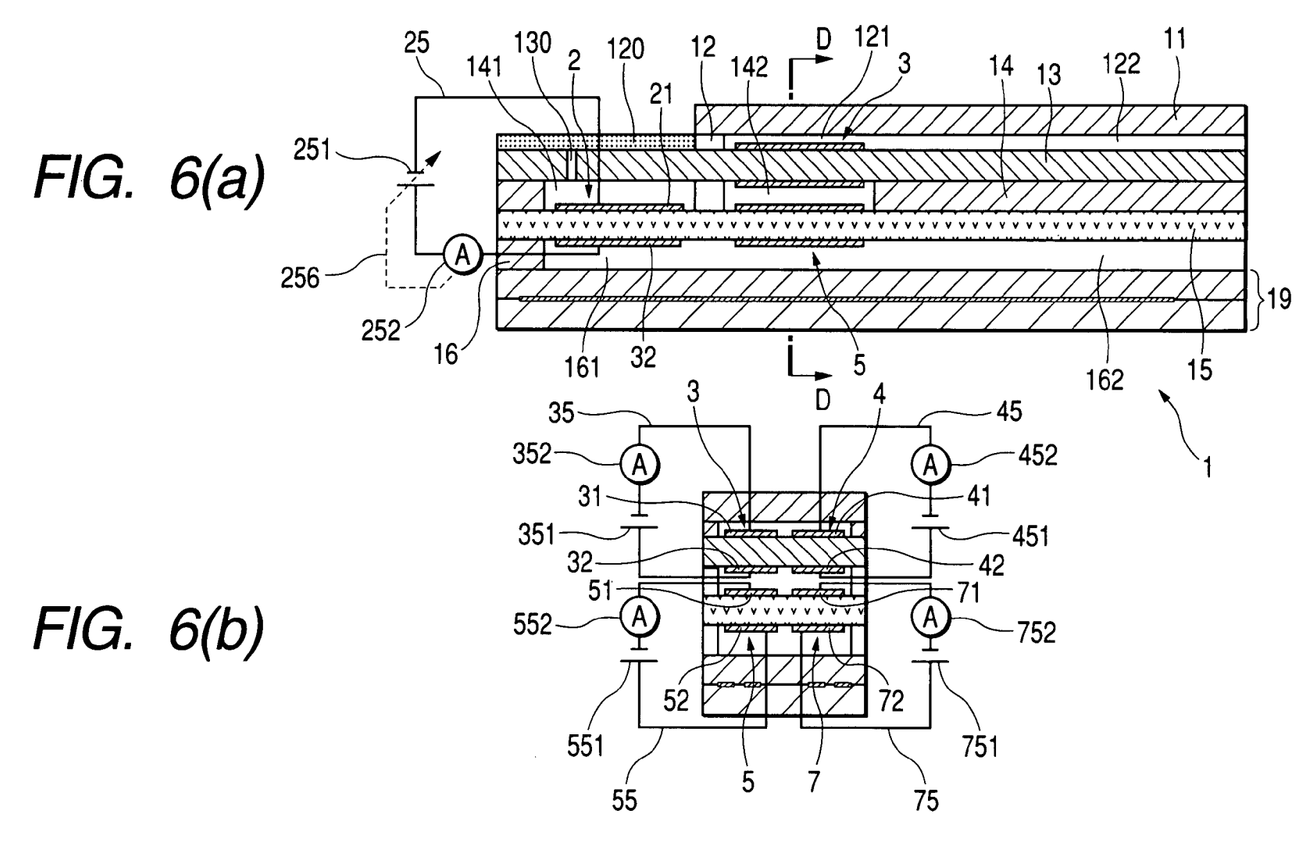
FIG. 6(a) is a longitudinal sectional view which shows a gas sensor element according to the fourth embodiment of the invention.
FIG. 6(b) is a transverse sectional view as taken along the line D—D in FIG. 6(a)

FIGS. 6(a) and 6(b) show the gas sensor element 1 according to the fourth embodiment of the invention which is equipped with a NOx measurement cell 7.

The NOx measurement cell 7 consists of a pair of electrodes 71 and 72 affixed to opposed surface of the oxygen ion-conductive solid electrolyte plate 15. The electrode 71 is exposed to the second measurement gas chamber 142, while the electrode 72 is exposed to the first reference gas chamber 161. The NOx measurement cell 7 connects electrically to a NOx measurement circuit 75 equipped with a power supply 751 and a current detector 752.

The electrode 71 is made of a Pt—Rh cermet that is active to decompose NOx. The power supply 751 applies the voltage (e.g., 0.40V) to the electrode 72 (a positive terminal). This causes the electrode 71 to reduce oxygen and NOx molecules within the second measurement gas chamber 142 to produce oxygen ions which are transferred or pumped to the electrode 72. The flow of current is, thus, produced in the NOx measurement cell 7 as a function of the concentration of NOx within the second measurement gas chamber 142.

The oxygen monitor cell 5 has the electrode 51 made of Pt—Au cermet which is inactive with respect to NOx or hardly dissociate NOx for minimizing a dissociated amount of NOx contained in the measurement gasses. Highly accurate measurement of concentration of NOx is, therefore, achieved by finding a difference between currents flowing through the oxygen monitor cell 5 and the NOx measurement cell 7 to minimize an error of the output from the NOx measurement cell 7 arising from the amount of oxygen molecules remaining within the second measurement gas chamber 142.

The gas sensor element 1 of this embodiment is, as apparent from the above discussion, designed to measure the concentration of NOx as well as the concentration of hydrocarbon and hydrogen gasses. Specifically, the gas sensor element 1 may be used in automotive vehicles to measure the concentration of air contaminants contained in exhaust emissions such as NOx, hydrocarbon, and hydrogen gasses simultaneously.

Other arrangements and operation are identical with those in the first embodiment, and explanation thereof in detail will be omitted here.

Figure 7A:
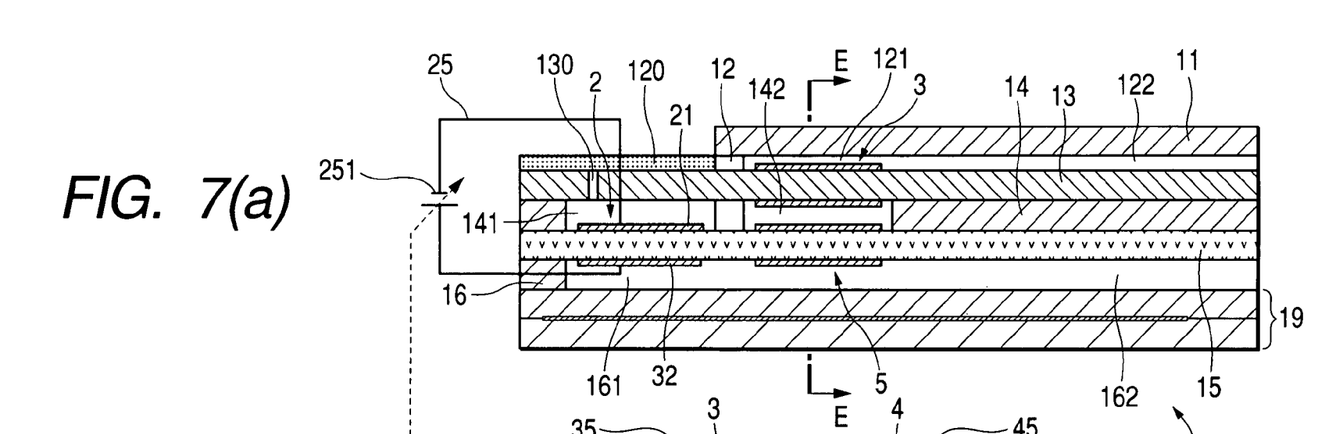
FIG. 7(a) is a longitudinal sectional view which shows a gas sensor element according to the fifth embodiment of the invention.
Figure 7B:
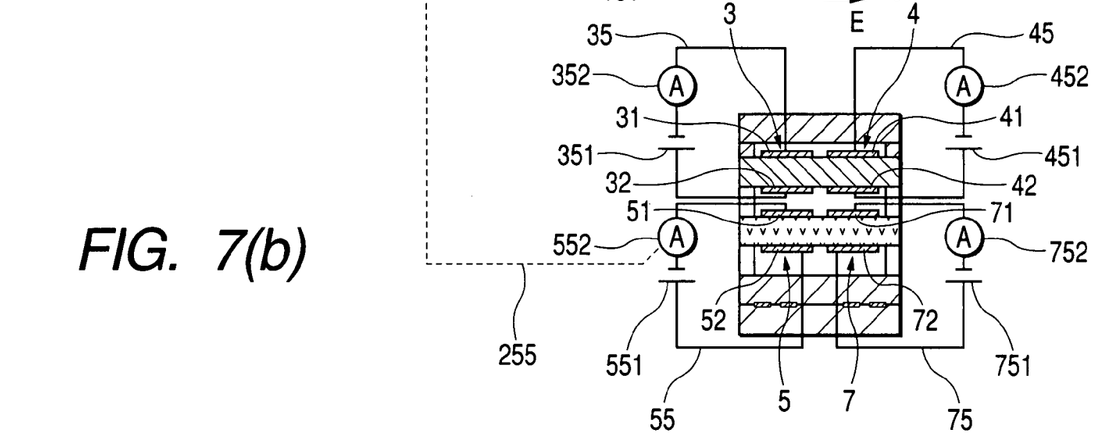
FIG. 7(b) is a transverse sectional view as taken along the line E—E in FIG. 7(a)

FIGS. 7(a) and 7(b) show the gas sensor element 1 according to the fifth embodiment of the invention which is different from the fourth embodiment in that the oxygen pump cell 2 is controlled using the current outputted by the oxygen monitor cell 5. This control is the same as that in the first embodiment, and explanation thereof in detail will be omitted here.

Other arrangements and operation are identical with those in the fourth, and explanation thereof in detail will be omitted here.

The gas sensor element 1 according to the sixth embodiment will be described below which is different from the above embodiments only in configuration of the first and second hydrogen-containing measurement gas cells 3 and 4. Other arrangements and operations are identical, and explanation thereof in detail will be omitted here.

The fist and second hydrogen-containing gas measurement cells 3 and 4 of this embodiment, like the above embodiments, each include the proton-conductive solid electrolyte plate 13 and a pair of electrodes affixed to the solid electrolyte plate 13 in the same position in the direction parallel to a flow of the measurement gasses.

Figure 8:
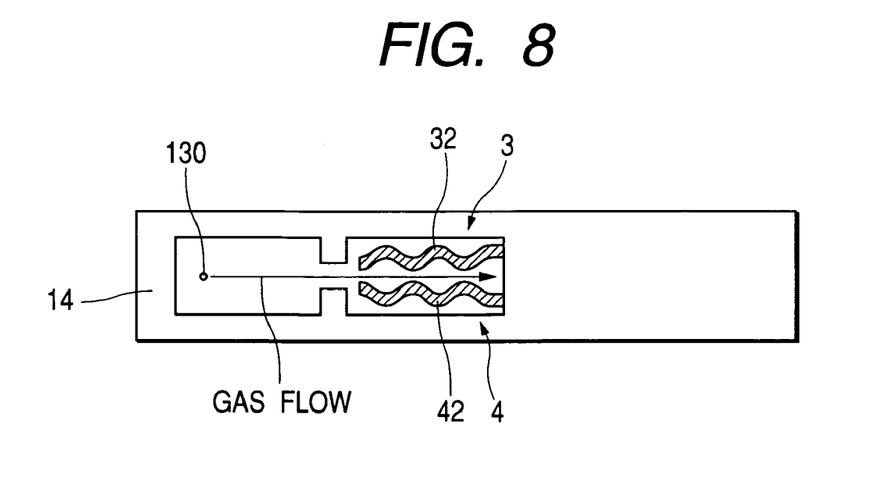
FIG. 8 is a horizontal sectional view which shows a first example of a structure of first and second hydrogen-containing gas measurement cells in the sixth embodiment of the invention.

FIG. 8 shows the first example of the sixth embodiment in which the electrode 32 of the first hydrogen-containing gas measurement cell 3 and the electrode 42 of the second hydrogen-containing gas measurement cell 4 are waved and extend in parallel to and symmetrically with respect to a flow of the measurement gasses (i.e., the lengthwise direction of the gas sensor element 1), as indicated by an arrow. Specifically, the electrode 32 is an mirror image of the electrode 42. The electrodes 32 and 42 are exposed to the second measurement gas chamber 142. The same electrodes (not shown) in configuration as the electrodes 32 and 42 are, like the above embodiments, affixed to an opposite surface of the solid electrolyte plate 13 exposed to the second reference gas chamber 121.

Figure 9:
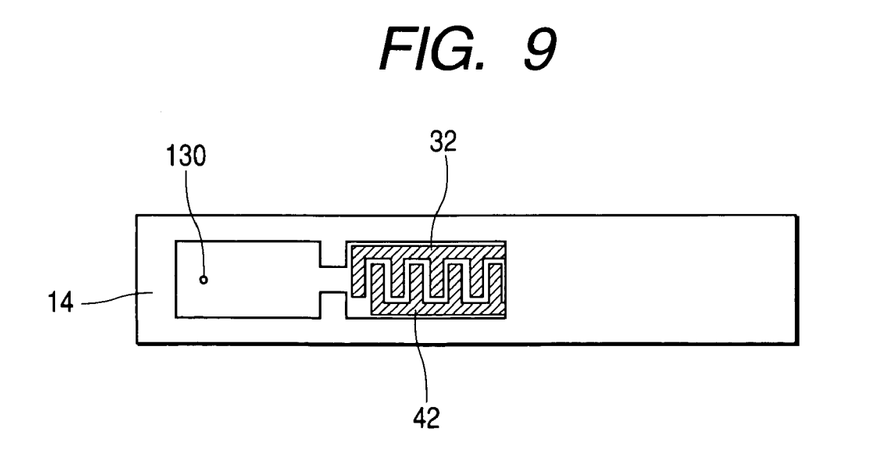
FIG. 9 is a horizontal sectional view which shows a second example of a structure of first and second hydrogen-containing gas measurement cells in the sixth embodiment of the invention.

FIG. 9 shows the second example in which the electrodes 32 and 42 are each of comb-shape and have teeth meshing with each other.

Figure 10:
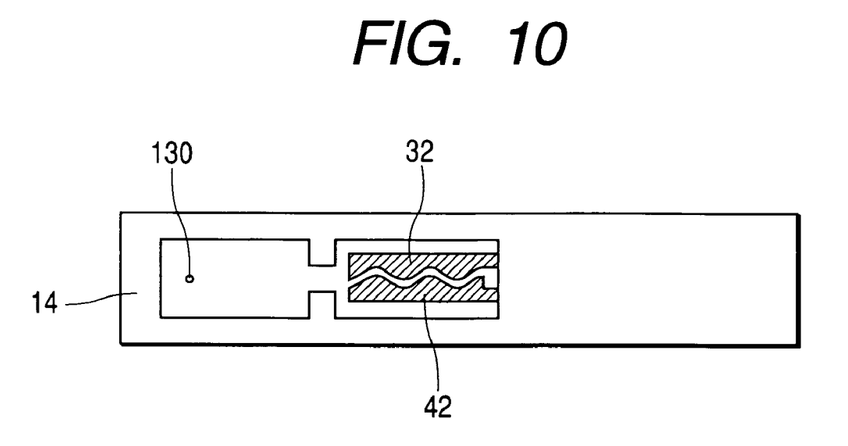
FIG. 10 is a horizontal sectional view which shows a third example of a structure of first and second hydrogen-containing gas measurement cells in the sixth embodiment of the invention.

FIG. 10 shows the third example in which the electrodes 32 and 42 have waved sides which so extend that the trough of each wave of the electrode 32 faces the crest of one of waves of the electrode 42.

Figure 11:
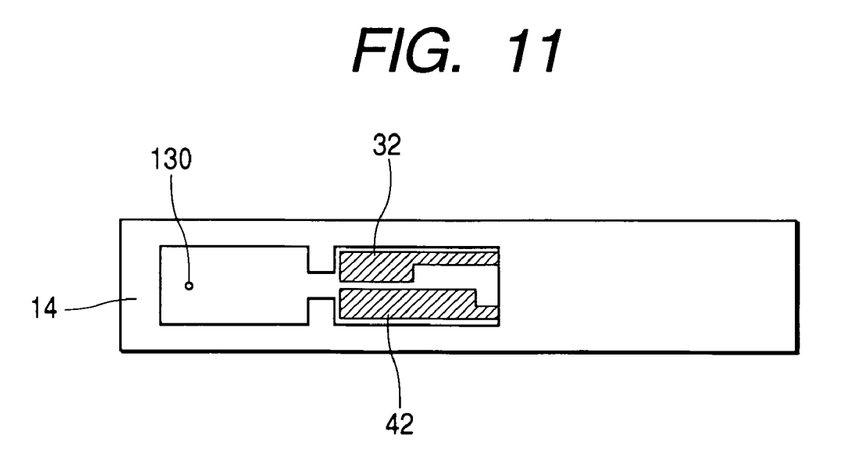
FIG. 11 is a horizontal sectional view which shows a fourth example of a structure of first and second hydrogen-containing gas measurement cells in the sixth embodiment of the invention.

FIG. 11 shows the fourth example in which the electrodes 32 and 42 are arrayed in the same position in the direction of flow of the measurement gasses, but difference in size or area thereof.

The electrodes 32 and 42 in the above examples are, as described above, arrayed in substantially the same position in the direction of flow of the measurement gasses, thereby achieving highly accurate measurement of concentration of hydrocarbon and hydrogen within the second measurement gas chamber 142 fee from a measurement error arising from the distribution of the hydrogen-containing gasses within the first and second measurement gas chambers 141 and 142.

In each of the above embodiments, the electrode 21 of the oxygen pump cell 2, the electrode 51 of the oxygen monitor cell 5, and the electrodes 32 and 42 of the first and second hydrogen-containing gas measurement cells 3 and 4 which are exposed to either of the first and second measurement gas chambers 141 and 142 may be made from a material containing in a principal component at least one of Pt, Pd, and Rh and at least one of Au, Cu, Pb and Ti. One of Au, Cu, Pb, and Ti may lie in content within a range of 1% to 30% of a total weight of each of the electrodes 21, 51, 32, and 42.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor element comprising:
   a measurement gas chamber into which measurement gasses enter, subjected to a given diffusion resistance;
   an oxygen pump cell working to control a concentration of oxygen contained in the measurement gasses within said measurement gas chamber, said oxygen pump cell including an oxygen ion-conductive solid electrolyte body and a first and a second oxygen pump electrode affixed to the oxygen ion-conductive solid electrolyte body, the first oxygen pump electrode being exposed to said measurement gas chamber; and
   a hydrogen-containing gas measurement cell working to measure a concentration of a hydrogen-containing gas contained in the measurement gasses within said measurement gas chamber, said hydrogen-containing gas measurement cell including a proton-conductive solid electrolyte body and a first and a second gas measurement electrode affixed to the proton-conductive solid electrolyte body, the first gas measurement electrode being exposed to said measurement gas chamber and adapted to produce a signal between the first and second gas measurement electrodes as a function of the concentration of the hydrogen-containing gas, the second gas measurement electrode being exposed to a reference gas chamber filled with a given reference gas.

2. A gas sensor element as set forth in claim 1, wherein said oxygen pump cell is located upstream of said hydrogen-containing gas measurement cell in a flow of the measurement gasses within said measurement gas chamber.

3. A gas sensor element as set forth in claim 1, further comprising a second hydrogen-containing gas measurement cell exposed to said measurement gas chamber.

4. A gas sensor element as set forth in claim 3, wherein said second hydrogen-containing gas measurement cell includes a proton-conductive solid electrolyte body and a first and a second gas measurement electrode affixed to the proton-conductive solid electrolyte body, the first gas measurement electrode being exposed to said measurement gas chamber and adapted to produce an electrical current between the first and second gas measurement electrodes as a function of a concentration of a hydrogen-containing gas contained within the measurement gasses which is different in kind from the hydrogen-containing gas to be measured by said hydrogen-containing gas measurement cell and wherein the concentration of the hydrogen-containing gas, as measured by said hydrogen-containing gas measurement cell, is indicated as a function of an electrical current produced between the first and second measurement electrodes of the hydrogen-containing gas measurement cell, and the concentration of the hydrogen-containing gas, as measured by said second hydrogen-containing gas measurement cell, is indicated as a function of a difference between the electrical currents produced by said hydrogen-containing gas measurement cell and said second hydrogen-containing gas measurement cell.

5. A gas sensor element as set forth in claim 4, wherein said hydrogen-containing gas measurement cell and said second hydrogen-containing gas measurement cell are arrayed in substantially the same position in the flow of the measurement gasses within said measurement gas chamber and symmetrical in configuration with respect to the flow of the measurement gasses.

6. A gas sensor element as set forth in claim 1, wherein the proton-conductive solid electrolyte body is formed by a perovskite type oxide made in matrix structure from at least one of $SrZrO_3$, $CaZrO_3$, $SrCeO_3$, and $BaCeO_3$.

7. A gas sensor element as set forth in claim 6, wherein one of Y, Yb, Sc, In, Gd, Dy, and Sm is substituted for either of Zr and Ce in the matrix structure of the proton-conductive solid electrolyte body.

8. A gas sensor element as set forth in claim 1, further comprising an oxygen monitor cell working to measure a concentration of oxygen in the measurement gasses.

9. A gas sensor element as set forth in claim 8, wherein said oxygen pump cell is so controlled as to keep an electrical current produced by said oxygen monitor cell constant.

10. A gas sensor element as set forth in claim 8, wherein said oxygen pump cell is so controlled as to keep a voltage developed in said oxygen pump cell constant.

11. A gas sensor element as set forth in claim 4, wherein voltages which are different in level from each other are applied to said hydrogen-containing gas measurement cell and said second hydrogen-containing gas measurement cell to produce outputs indicative of the concentrations of the hydrogen-containing gasses.

12. A gas sensor element as set forth in claim 1, wherein the first oxygen pump electrode of said oxygen pump cell and the first gas measurement electrode of said hydrogen-containing gas measurement cell which are exposed to said measurement gas chamber are each made of a material which is low in oxidizing activity.

13. A gas sensor element as set forth in claim 8, wherein said oxygen monitor cell includes an oxygen ion-conductive solid electrolyte body and a first and a second monitor electrodes affixed to the oxygen ion-conductive solid electrolyte body, the first monitor electrode being exposed to said measurement gas chamber and made of a material which is low in oxidizing activity.

14. A gas sensor element as set forth in claim 13, wherein the first oxygen pump electrode of said oxygen pump cell, the first gas measurement electrode of said hydrogen-containing gas measurement cell, and the first pump electrode of said oxygen monitor cell which are exposed to said measurement gas chamber are each made from a material containing in principal component at least one of Pt, Pd, and Rh and at least one of Au, Cu, Pb and Ti.

15. A gas sensor element as set forth in claim 14, wherein one of Au, Cu, Pb, and Ti lies in content within a range of 1 to 30% of a total weight of each of the electrodes.

16. A gas sensor element as set forth in claim 1, further comprising a NOx measurement cell which includes an oxygen ion-conductive solid electrolyte body and a first and a second NOx measurement electrodes affixed to the oxygen ion-conductive solid electrolyte body, the first NOx measurement electrode being exposed to said measurement gas chamber and active with NOx contained in the measurement gasses, said NOx measurement cell producing an electrical current as a function of a concentration of NOx contained in the measurement gasses.

17. A gas sensor element as set forth in claim 16, further comprising an oxygen monitor cell working to produce an electrical current as a function of a concentration of oxygen within said measurement gas chamber, and wherein a difference between the electrical currents produced by said oxygen monitor cell and said NOx measurement cell is used for determining the concentration of NOx contained in the measurement gasses.

18. A gas measuring method comprising the steps of:

introducing measurement gasses into a measurement gas chamber while being subjected to a given diffusion resistance;

controlling an electrical current flowing through an oxygen pump cell made up of an oxygen ion-conductive solid electrolyte body and a first and a second pump electrode affixed to the oxygen ion-conductive solid electrolyte body to pump oxygen molecules selectively into and out of the measurement gas chamber to regulate a concentration of oxygen within the measurement gas chamber, the first pump electrode being exposed to the measurement gas chamber; and measuring an electrical current flowing through a hydrogen-containing gas measurement cell made up of a proton-conducive solid electrolyte body and a first and a second gas measurement electrode affixed to the proton-conductive solid electrolyte body to determine a concentration of a given hydrogen-containing gas contained in the measurement gasses, the first gas measurement electrode being exposed to the measurement gas chamber, the second gas measurement electrode being exposed to a reference gas chamber filled with a given reference gas.

19. A gas measuring method comprising the steps of:

introducing measurement gasses into a measurement gas chamber while being subjected to a given diffusion resistance;

controlling an electrical current flowing through an oxygen pump cell made up of an oxygen ion-conductive solid electrolyte body and a first and a second pump electrode affixed to the oxygen ion-conductive solid electrolyte body to pump oxygen molecules selectively into and out of the measurement gas chamber to regulate a concentration of oxygen within the measurement gas chamber, the first pump electrode being exposed to the measurement gas chamber;

measuring an electrical current flowing through a first hydrogen-containing gas measurement cell made up of a proton-conducive solid electrolyte body and a first and a second gas measurement electrode affixed to the proton-conductive solid electrolyte body to determine a concentration of a first hydrogen-containing gas contained in the measurement gasses, the first gas measurement electrode being exposed to the measurement gas chamber, the second gas measurement electrode being exposed to a reference gas chamber filled with a given reference gas; and measuring an electrical current flowing through a second hydrogen-containing gas measurement cell made up of a proton-conducive solid electrolyte body and a first and a second gas measurement electrode affixed to the proton-conductive solid electrolyte body to determine a concentration of a second hydrogen-containing gas contained in the measurement gasses, the first gas measurement electrode being exposed to the measurement gas chamber, the second gas measurement electrode being exposed to a reference gas chamber, the second hydrogen-containing gas being different in kind from the first hydrogen-containing gas.

* * * * *